United States Patent
Mühlhoff et al.

(10) Patent No.: US 7,692,865 B2
(45) Date of Patent: Apr. 6, 2010

(54) ADAPTER FOR COUPLING A LASER PROCESSING DEVICE TO AN OBJECT

(75) Inventors: Dirk Mühlhoff, Kunitz (DE); Elke Ebert, Jena (DE); Karsten Festag, Jena (DE); Uwe Wolf, Magdala (DE)

(73) Assignee: Carl Zeiss Meditec AG, Jena (DE)

(*) Notice: Subject to any disclaimer, the term of this patent is extended or adjusted under 35 U.S.C. 154(b) by 605 days.

(21) Appl. No.: 10/579,439

(22) PCT Filed: Oct. 18, 2004

(86) PCT No.: PCT/EP2004/011785
§ 371 (c)(1),
(2), (4) Date: Feb. 27, 2007

(87) PCT Pub. No.: WO2005/048896
PCT Pub. Date: Jun. 2, 2005

(65) Prior Publication Data
US 2007/0253083 A1 Nov. 1, 2007

(30) Foreign Application Priority Data
Nov. 14, 2003 (DE) .................. 103 53 264

(51) Int. Cl.
G02B 27/14 (2006.01)
(52) U.S. Cl. ...................... 359/634; 359/819
(58) Field of Classification Search .............. 359/618, 359/634, 819; 351/221; 385/39
See application file for complete search history.

(56) References Cited

U.S. PATENT DOCUMENTS

| | | | |
|---|---|---|---|
| 4,558,698 A | 12/1985 | O'Dell | |
| 5,548,352 A * | 8/1996 | Dewey | ............ 351/160 H |
| 5,549,632 A | 8/1996 | Lai | |
| 5,984,916 A | 11/1999 | Lai | |
| 6,254,595 B1 | 7/2001 | Juhasz et al. | |
| 6,373,571 B1 | 4/2002 | Juhasz et al. | |
| 2001/0021844 A1 | 9/2001 | Kurtz et al. | |
| 2002/0103481 A1 | 8/2002 | Webb et al. | |
| 2002/0103482 A1 | 8/2002 | Scholler et al. | |

FOREIGN PATENT DOCUMENTS

EP 1 159 986 A2 12/2001

* cited by examiner

*Primary Examiner*—Joseph Martinez
(74) *Attorney, Agent, or Firm*—Patterson, Thuente, Skaar & Christensen, P.A.

(57) ABSTRACT

An adapter for coupling a laser processing device to an object, said adapter having a central region which can be moved into the beam path of the laser processing device, an illumination beam path through which illumination radiation can be guided for illumination of an object field which can be covered by the central region, and a peripheral region located outside the central region and by which the adapter can be mounted on the object and/or on the laser processing device, wherein the illumination beam path extends in the peripheral region and guides illumination radiation, coupled into the peripheral region, to the object field direct and/or via the central region.

19 Claims, 5 Drawing Sheets

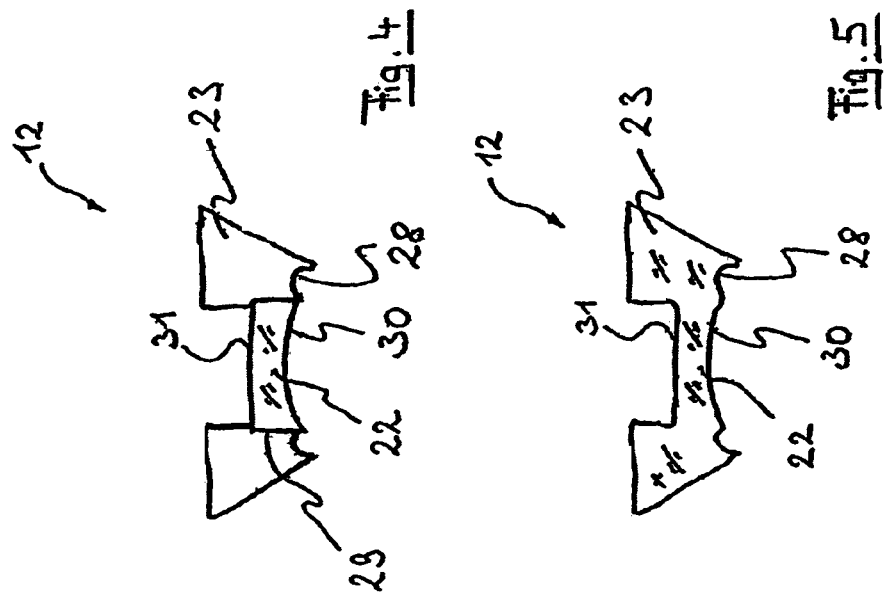
Fig. 4
Fig. 5
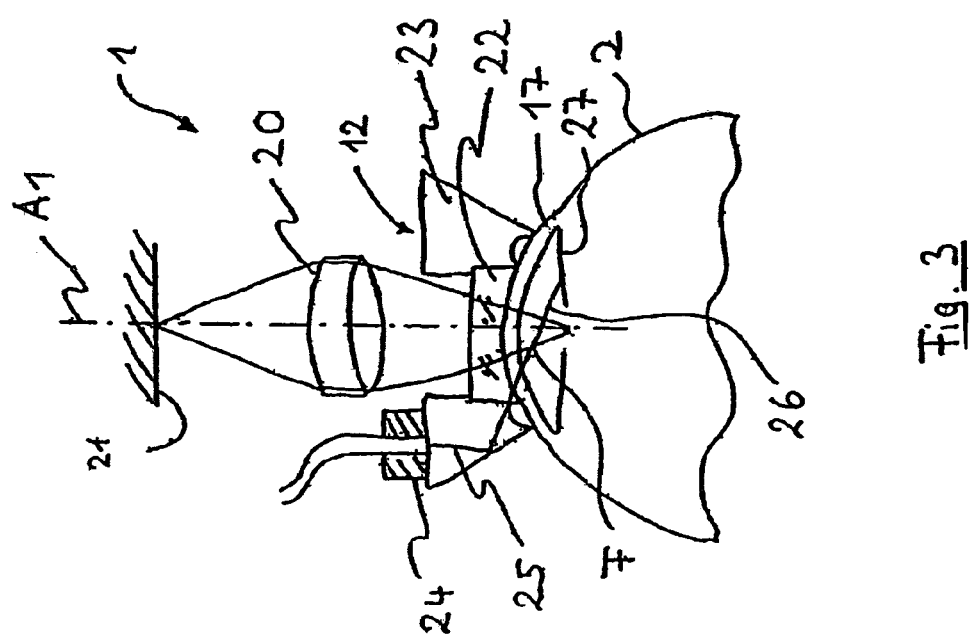
Fig. 3

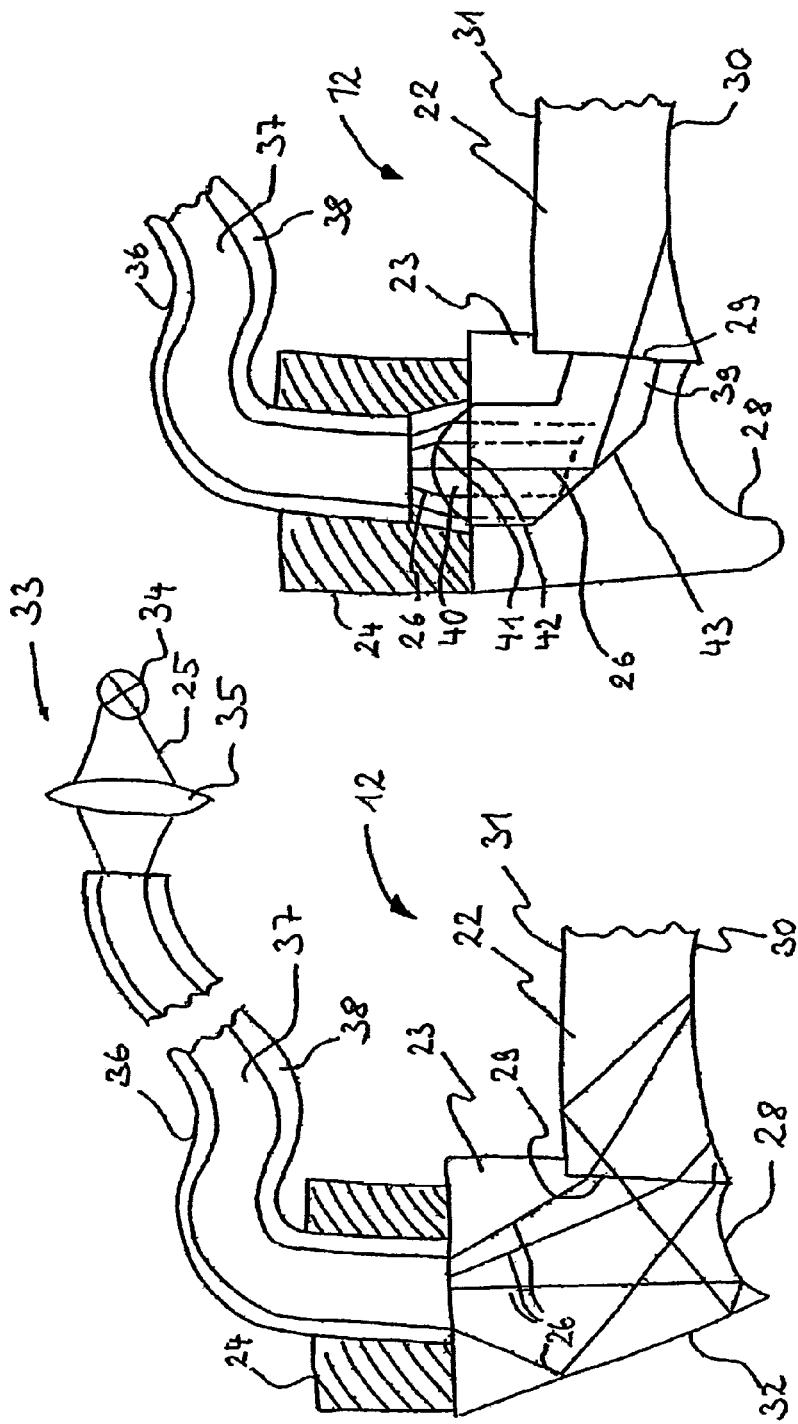

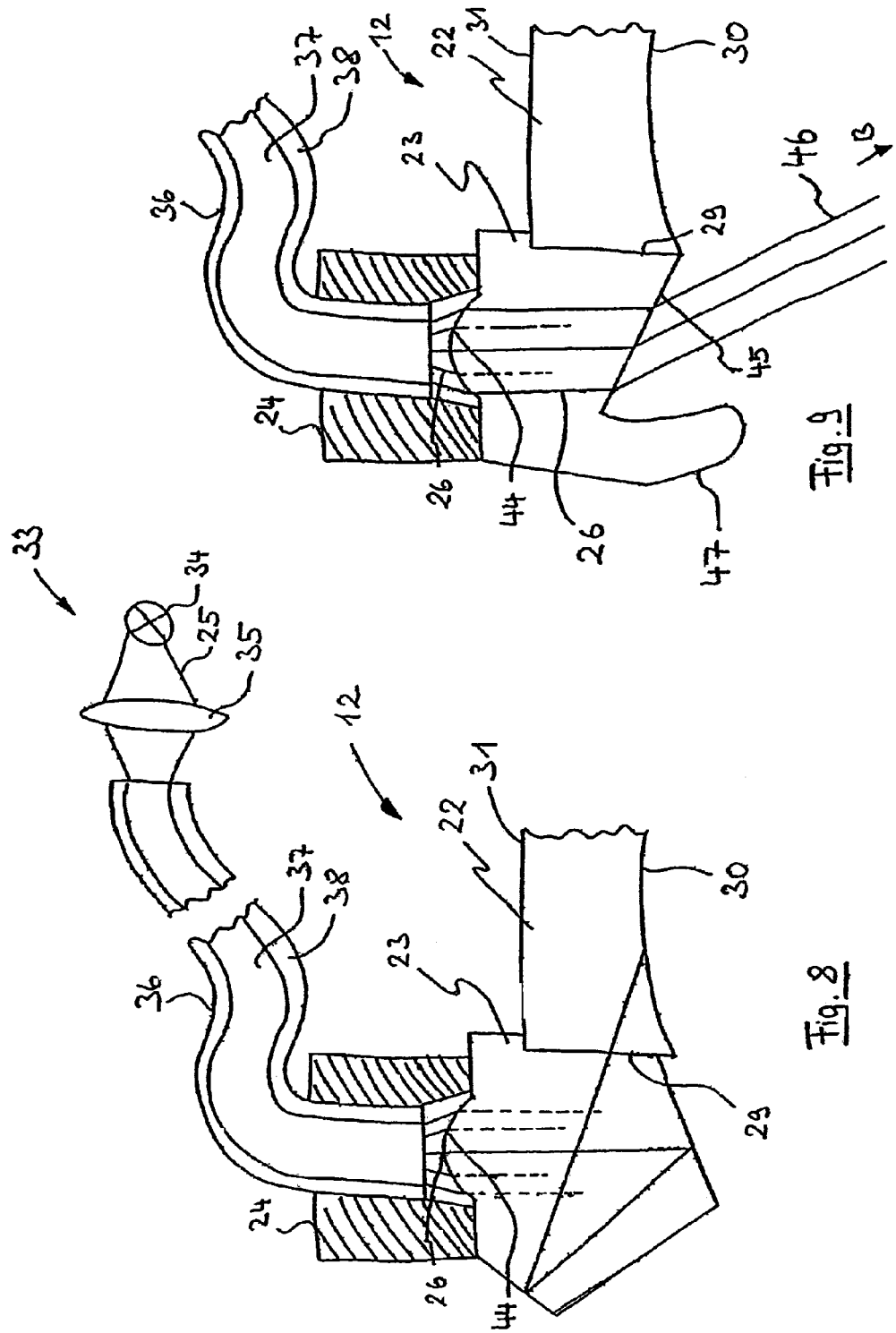

ADAPTER FOR COUPLING A LASER PROCESSING DEVICE TO AN OBJECT

FIELD OF THE INVENTION

The invention relates to an adapter for coupling a laser processing device to an object, said adapter comprising a central region which can be switched into the beam path of the laser processing device, an illumination beam path through which the illumination radiation for illumination of an object field detectable by the central region can be guided, and a peripheral region located outside the central region, by which peripheral region the adapter can be mounted on the object and/or on the laser processing device.

BACKGROUND OF THE INVENTION

For materials processing by means of laser radiation, a laser processing device is employed in many cases for scanning the areas of the object which are to be processed with the laser beam. The precision in positioning the laser beam usually determines the precision achieved in processing. Exact three-dimensional positioning is required when focusing the laser beam into a processing volume. For high-precision processing, it is usually indispensable, therefore, to hold the object in an exactly defined position relative to the laser processing device. For such applications, the above-mentioned adapter is useful, because it enables fixation of the object to be processed, so that defined ratios can be achieved up to the processing volume. The central region of the adapter thus becomes part of the beam path.

This is necessary, in particular, in micro-processing of materials which have only low linear optical absorption in the spectral range of the processing laser radiation. In such materials, usually non-linear interactions between the laser radiation and the material are utilized generally in the form of an optical breakthrough being generated in the focus of the laser beam. Since the processing effect then only occurs in the laser beam focus, exact three-dimensional positioning of the focal point is indispensable. Thus, exact depth adjustment of the focal position in the beam path is required in addition to two-dimensional deflection of the laser beam. The above-mentioned adapter serves to ensure constant optical conditions and ones that are known with a certain precision in the beam path leading to the object by the central region of the adapter being part of the beam path and the adapter coupling the object and the laser processing device.

A typical application for such an adapter is the ophthalmic surgery method known as femtosecond LASIK, wherein the laser processing device focuses a laser beam to a focal point on the order of a few micrometers into the cornea. A plasma causing local separation of corneal tissue is then generated in the focus. By suitable sequential arrangement of the zones of local separation thus generated, macroscopic cuts are realized and a determined partial volume of the cornea is isolated. Then, by removal of said partial volume, a desired change in refraction of the cornea is achieved, thus enabling correction of defective eyesight.

For this LASIK method, a contact lens provided with reference marks is known from U.S. Pat. No. 6,373,571. This contact lens is adjusted by means of a separate measurement device, thus leading to a relatively complex design. An example of an adapter of the aforementioned type is described in EP 1 159 986 A2. While being similar to the contact lens of U.S. Pat. No. 6,373,571, it additionally comprises a periphery as well in the form of a holder having hair marks, which allow visual alignment by the surgeon.

In materials processing by means of laser radiation, there often arises the need to monitor execution of processing. It is desired to be able to observe the processing field during application of the laser radiation. This holds true, in particular, for the aforementioned LASIK method wherein the treating physician has to observe the field of operation. Therefore, the aforementioned laser processing device usually comprises an optical system for imaging the area to which the laser radiation is applied. The image is generated either on a camera or in an intermediate image plane from which direct visual inspection through an eyepiece is then possible. Observation is effected through the central region of the adapter, and it is required for the laser processing device to illuminate the area to which the laser radiation is being applied and which is being observed as the object field.

As the illumination necessary for visual observation, the use of a light source whose radiation passes through the laser processing device could be contemplated. However, since the optics provided therein usually comprise a multiplicity of interfaces all having a certain residual reflectivity, a non-negligible part of the illumination radiation inevitably crosstalks into the image of the object field. Depending on the optical arrangement, this is noticeable in the image plane as global brightening of the image or as bright spots at fixed sites of the observed object field, especially at its center. In any case, the reflections reduce the image quality with which the object field can be observed.

A further approach (not disclosed up to now) would be conceivable in the form of pupil separation. This would then require to first image the light source used for illumination into a pupil plane of the optical system of the laser processing device. In doing so, the image would have to be designed such that only an outer ring of the pupil plane guides illumination radiation and the center of the pupil plane is used only for imaging the object field. The reflectivity of objects located near the image plane could then not impair imaging of the object field. However, the condition that all reflecting surfaces should be located near an image plane can usually not be satisfied by an adapter of the aforementioned type, because its central region is inevitably located in the beam path, and the position of the adapter and, consequently, of the possibly reflecting surfaces is given by the type of the object and is, thus, hardly variable and, in particular, not optimally selectable under optical aspects. Also, in pupil separation as described above, interfering parasitic radiation would have to be expected.

SUMMARY OF THE INVENTION

Therefore, it is the object of the invention to provide an adapter of the aforementioned type such that illumination of the object field is possible in a simple manner without impairing the quality of the object field covered by the observation beam path.

This object is achieved by an adapter of the type mentioned above, wherein the illumination beam path is guided in the peripheral region and carries illumination radiation coupled in at the peripheral region to the object field directly and/or via the central region.

It is also an essential concept of the invention to separate the illumination beam path and the observation beam path such that no undesired reflections can occur. In this way, good image quality is achievable. The invention avoids the introduction of illumination light via the same elements as those used for observation. Instead, the peripheral region which is neither involved in nor intended for imaging of the object field is used to couple the illumination radiation into the adapter.

The illumination radiation is fed at the peripheral region. This largely prevents back reflections into the observation beam path of the image. It is thus not excluded that the treatment radiation supplied at the peripheral region is also carried via the central region of the adapter, which central region is involved in imaging. Interference with imaging can be avoided almost completely by supplying the radiation via the peripheral region.

The adapter according to the invention allows to achieve secure coupling between the laser processing device and the object and, at the same time, good-quality optical observation of the object. Therefore, the adapter is particularly suitable for surgical methods, in particular at the eye. For this application, a design is advantageous wherein the central region comprises a contact glass to be placed on the object and the peripheral region is a mount for the contact glass. In order to carry out the surgical method, such contact glass is usually placed on the eye and fixed there, e.g. by a vacuum. To ensure good optical quality of the contact glass, it is convenient to effect vacuum fixation at the mount. Therefore, it is convenient to provide a corresponding fixing device on the side of the mount facing the object, said fixing device allowing the adapter to be fixed to the object. If vacuum fixation is used, the mount may comprise suitable suction ducts in order to suck the adapter to the eye by vacuum.

The optical properties of the contact glass are defined by its front and rear surfaces, i.e. the rear surface facing the object and the front surface facing the laser processing device. Both surfaces may either be plane or may be provided with a convex or concave curvature or may even be aspherical. The contact glass has to be transparent for the radiation of the laser processing device. This applies to both the observation radiation and to treatment radiation possibly applied by the laser processing device. Therefore, suitable materials are conventional optical glasses, but also transparent plastics of optical quality, e.g. PMMA, zeonex, etc.

The illumination radiation for the object field is introduced at the peripheral region, e.g. the mount. In a variant having a particularly simple design, the mount may comprise a material which is transparent for the illumination radiation, in particular PMMA, polycarbonate, zeonex or HW 55.

The function of the adapter may be to impart to that surface of the object which faces the laser processing device a determined shape or to provide a known interface. However, the above-mentioned LASIK method further requires to couple the adapter in a predetermined mechanical position with the laser processing device, which is then provided as a laser therapy apparatus. This is also done via the peripheral region which, as mentioned, may be provided, for example, as a mount for a contact glass. In this embodiment, the input side of the adapter which is oriented toward the laser processing device is, therefore, preferably provided with suitable means for secure connection to the output (e.g. the distal end) of the laser processing device or of its optical system, said output being oriented toward the object, and thus secure fixation relative to the laser processing device is possible by means of a locking mechanism. For a locking mechanism the provision of a flange surface in the peripheral region is suitable, for example.

In order to guide the illumination radiation to the object field, it is convenient to provide a special coupling unit for illumination radiation in the peripheral region. Said unit may be, for example, a coupler for a light wave guide supplying the illumination radiation.

Advantageously, in order to allow the illumination radiation to be optimally guided to the object field, the coupling unit may be provided to have an imaging effect, in particular by a convex, concave, cylindrical or toroidal interface. Alternatively or additionally, in order to realize certain spectral properties for illumination of the object field, the coupling unit may comprise a dielectric coat or absorbing filters, e.g. colored glasses, for the purpose of spectral filtering or reduction of reflections.

The illumination radiation introduced into the peripheral region may be generated by suitable light sources and guided to the object field by light guiding means. Such light guiding means are simply realized by reflecting surfaces. Therefore, it is convenient to provide the peripheral region with at least one surface reflecting the illumination radiation. It is also conceivable to provide the peripheral region with light guiding channels reflecting the illumination radiation. A particularly simple realization consists in a reflecting external surface, which conveniently allows to utilize the principle of total internal reflection in order to guide illumination radiation, introduced at the peripheral region, to the object field.

In a variant of the adapter according to the invention, a transparent plastic mount into which a contact glass, e.g. a plano-concave contact glass, is glued may be used. Said mount serves as a mechanical connection between the contact glass and the laser processing device provided as a therapeutic apparatus. The contact glass may be glued into the mount with an optically transparent adhesive, so that the interface between the contact glass and the mount is optically transparent. It is particularly advantageous if the refractive index of the adhesive comprises a refractive index located between that of the material of the mount and that of the material of the contact glass, because reflection losses at the transition of the illumination radiation from the mount into the contact glass are thus minimal. For further reduction of losses, optically active dielectric coats can be applied to the interfaces of both the mount and the contact glass.

If a coupling port for a light wave guide is provided to the mount, the illumination radiation from a light source, e.g. from a thermionic emission radiator or a light emitting diode, may be simply coupled in via a light wave guide. In a convenient further embodiment, light wave guide bundles are used. The coupling-in may use, for example, an ellipsoid mirror as known to the person skilled in the art. The position of the point of entrance may be located almost anywhere at the peripheral region. The radiation is guided within the mount by suitable reflection, e.g. by total internal reflection, until it is incident on the interface to the contact glass. Here, the radiation is coupled into the contact glass. If the contact glass contacts the eye to be treated, the radiation is now coupled into the cornea and is guided into deeper levels of the eye from there. When impinging on the iris or on scattering centers caused by the laser therapy, the radiation is scattered and can be imaged via the observation beam path of the laser processing device, i.e. via the contact glass and the optics of the laser processing device.

In a modification, a plurality of coupling units are used, because then uniform illumination of the object field can be achieved. If the variant with reflecting surfaces is used in combination with a plurality of coupling units, the reflecting surfaces can be segmented into facets, and each coupling unit can have one facet or group of facets assigned to it. In addition, selective illumination of the object field is increased when separately controlling the light sources feeding light to the coupling units. For example, illumination modes are realizable wherein the light selectively irradiates the object field only from one side.

By designing the reflecting surfaces or, generally, the guidance of the illumination radiation in the peripheral region to have an imaging effect, selective collimation of light which propagates, for example, in a diverging manner from the light guide exit may be achieved. In particular, it is possible to use spherical surfaces. An oblique incidence of the light on this surface may result in an astigmatism which can be selectively used to form the light such that the angle of divergence is very small in a section plane parallel to the optical axis of the observation beam path, but is very great perpendicular thereto. The entire object field is thus effectively illuminated in a plane perpendicular to the optical axis of the laser processing device, i.e. to the axis of its observation beam path.

In an optional embodiment, the peripheral region may comprise a separate exit surface for illumination radiation, said surface enabling illumination of an object still spaced apart from the adapter, in particular, of course, the human eye in the case of a LASIK therapy apparatus, said object not yet contacting the central region, e.g. the contact glass, of the adapter. This may be important for adjustment of the object relative to the optical axis of the laser processing device. This further exit surface may, of course, also have a determined imaging effect by designing a determined surface shape or property. For example, spherical surface shapes allowing an end surface of a light guide to be imaged into a specific plane are particularly advantageous. Alternatively, a toroidal shape or the shape of a circumferential ridge may be used, which is very easy to realize by rotary processing of the material of the adapter. Moreover, such toroidal shape advantageously leads to the illumination radiation spreading out and thus causes uniform illumination of the object field, even if the object does not yet contact the central region of the adapter.

The exit surface above which the illumination radiation at the peripheral region of the adapter is guided to the object directly or via the central region, may be alternatively or partially designed as a scattering surface. Thus, a particularly strong homogenization of the illumination radiation at the object field is achieved.

In order to achieve a particularly compact design, it is advantageous to provide the coupling unit with an LED attached to the peripheral region or embedded therein. This alternative to a light guide leads to a very compact design. The LED may be glued or cast directly into the peripheral region, e.g. a mount for a contact glass. Suitable corresponding terminals are provided for contacting the LED.

Of course, this concept is not limited to the use of a single LED, and several LEDs may be used as well, with the possibility of controlling all LEDs via a pair of terminals or to connect each LED individually via separate electrical terminals. It is also possible to gather LEDs in groups and to provide each group with its own contacts.

It is particularly advantageous to provide the terminals as annular contact surfaces. This has the advantage that the adapter can be attached in any rotary position and that the LEDs can be contacted in any position. It is not stringently required to provide the annular contact surface on the adapter's side; alternatively, it is also possible to use suitable annular contacts at the processing device.

In a further embodiment for contacting the LED, current is supplied without mechanical contacts. Instead, inductive or capacitive coupling is employed. For this purpose, a suitable coil is provided, which may be mounted, for example, on the laser processing device. The coil generates an alternating electromagnetic field inducing an alternating voltage in a coil provided in the peripheral region of the adapter, by which alternating current the LED is operated. In the same manner, capacitive energy transmission is also possible. For this purpose, it is useful to provide two large conductive surfaces on the adapter and on the feeding unit, which surfaces are directly opposite each other in pairs and form an electrical capacitor. Energy transmission to the LED is achieved by applying an alternating field.

Suitable LEDs are white-light LEDs or color LEDs. In the case of color LEDs, it is convenient to gather LEDs in groups, e.g. to assemble each group from red, green and blue LEDs. If the red, green and blue LEDs are individually controllable, the color temperature of illumination may be adjusted via such control. This makes it possible to particularly emphasize certain structures, such as blood vessels, for example, by changing the color temperature of the illumination radiation, e.g. to green illumination.

If it is desired to manufacture the adapter at least partially from non-transparent materials, a multi-part design comprising a non-transparent material for the mount and a transparent material for the contact glass will usually be selected. A suitable non-transparent material for the peripheral region is, for example, metal or ceramics, which have superior strength and elasticity as compared with plastics. Suitable optical elements guiding the illumination radiation to the object field to be illuminated are then provided within such metal mount. The latter may be, for example, a reflecting bore which transmits observation radiation supplied at the peripheral region. The bore may comprise mirror-coated internal surfaces and may thus guide the observation beams by multiple reflection. Angular designs of the bore are also possible. The bore may terminate either at the interface which extends from the mount to the contact glass, or in the lower region of the mount so that the guided light exits and irradiates a plane below the contact glass. As an alternative or in addition, an imaging element, such as a suitable lens, may also be provided within the bore.

In order to achieve particularly low costs of manufacture, it is possible and advantageous to realize the peripheral region and the central region integrally in a single component. Thus, for example, injection molding techniques are suitable for manufacture.

BRIEF DESCRIPTION OF THE DRAWINGS

The invention will be explained in more detail below, by way of example and with reference to the drawings, wherein

FIG. 3 shows a schematic view of the illumination and observation beam paths in an adapter for an ophthalmic method;

FIG. 4 shows a schematic sectional view of an adapter for an ophthalmic method realized as a contact glass comprising a mount;

FIG. 5 shows a schematic sectional view of an integrally formed adapter for a surgical method;

FIG. 6 shows a schematic sectional view illustrating the illumination beam path in an adapter for an ophthalmic method;

FIG. 7 shows an adapter having a modified design as compared with FIG. 6;

FIG. 8 shows a further modified adapter;

FIG. 9 shows a sectional view of an adapter for an ophthalmic method, wherein illumination of the object field is possible already before positioning on the eye.

DETAILED DESCRIPTION OF THE DRAWINGS

Figure 1:
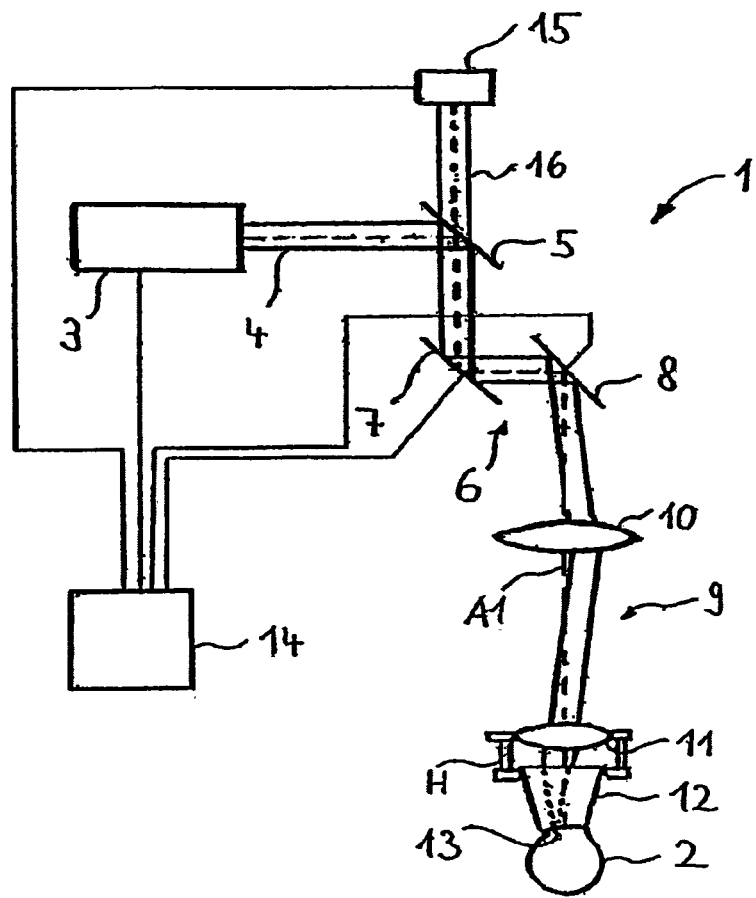
FIG. 1 shows a schematic view of a laser processing device for an ophthalmic method.

FIG. 1 shows a treatment apparatus for an ophthalmic method similar to that described in EP 1 159 986 A1 or in U.S. Pat. No. 5,549,632. The treatment apparatus 1 of FIG. 1 serves to effect correction of defective eyesight on the eye 2 of a patient according to the known LASIK method. For this purpose, the treatment apparatus 1 comprises a laser 3 which emits pulsed laser radiation. The pulse duration is e.g. in the femtosecond range, and the laser radiation acts by means of non-linear optical effects in the cornea in the manner described above. The treatment beam 4 emitted by the laser 3 along an optical axis A1 is incident on a beam splitter 5 which guides the treatment beam 4 to a scanning unit 6. The scanning unit 6 comprises two scanning mirrors 7 and 8 which are rotatable about mutually orthogonal axes such that the scanning unit 6 two-dimensionally deflects the treatment beam 4. Adjustable projection optics 9 focus the treatment beam 4 onto or into the eye 2. The projection optics 9 comprise two lenses 10 and 11. The treatment apparatus 1 represents a laser processing device.

Following the lens 11, there is arranged an adapter 12 which is permanently connected to the lens 11, and thus to the beam path of the treatment apparatus 1, by a holder H. The adapter 12, which will be described in more detail later, contacts the cornea of the eye 2. The optical combination of the treatment apparatus 1 with the adapter 12 attached to it causes the treatment beam 4 to be focused in a focus 13 located in the cornea of the eye 2.

Like the laser 3 and the projection optics 9, the scanning unit 6 is also controlled by a control apparatus 14 via control lines (not specified in detail). The control apparatus 14 determines the position of the focus 13 both transverse to the optical axis A1 (by the scanning mirrors 7 and 8) and along the optical axis A1 (by the projection optics 9).

The control apparatus 14 further reads out a detector 15 which reads out the radiation scattered back by the cornea and passing through the beam splitter 5 as back reflection radiation 16. The detector 15 allows very exact control of the operation of the laser 3.

The adapter 12 ensures that the cornea of the eye 2 obtains a desired intended shape. Due to the cornea 17 contacting the adapter 12, the eye 2 is in a predetermined position to the adapter 12 and thus to the treatment apparatus 1 connected to it.

Figure 2:
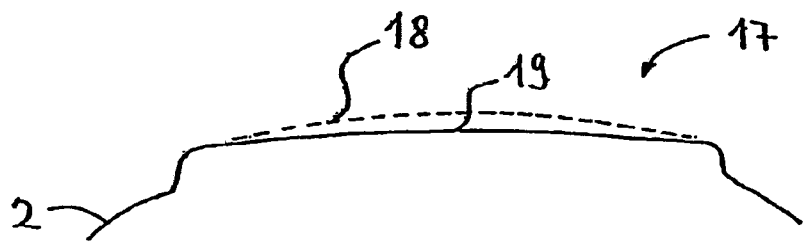
FIG. 2 shows a schematic view of the cornea of a patient's eye.

This is schematically shown in FIG. 2 showing a sectional view of the cornea 17. In order to achieve exact positioning of the focus 13 in the cornea 17, the curvature of the cornea 17 has to be taken into account. The cornea 17 has an actual shape 18 which differs from one patient to another. Now, the adapter 12 contacts the cornea 17 such that it deforms the latter toward a desired intended shape 19. The exact profile of the intended shape 19 depends on the curvature of the surface of the adapter 12 facing the eye 2. Known geometric and optical conditions for introducing and focusing the treatment beam 4 in the cornea 17 are given by the adapter 12. Since the cornea 17 is in contact with the adapter 12, which is in turn stationary relative to the beam path of the treatment apparatus 1 due to the holder H, the focus 13 can be exactly positioned three-dimensionally in the cornea 17 by the control of the scanning unit 6 and the adjustable projection optics 9.

With the treatment apparatus 1, it is required that the physician observe the field of operation, i.e. the cornea 17, during therapy. Therefore, the optical system schematically represented in FIG. 3 is provided for imaging the field of operation. In addition to the laser beam arrangement, an observation microscope 20 (not shown in FIG. 1 for the sake of simplicity) is additionally integrated into the treatment apparatus 1, which microscope images an object field F of the eye 2 onto a receiver 21. The receiver 21 may be realized as a CCD camera, for example. Of course, an eyepiece focused on an intermediate image plane may also be employed instead of the receiver 21. For illumination of the observation microscope 20, the adapter 12 is designed to direct illumination radiation onto the object field F. For this purpose, the adapter 12 has a two-part structure. It comprises a contact glass 22 contacting the cornea 17 and imparting to it the desired shape, as well as a mount 23 for the contact glass 22. The mount 23 comprises a coupler 24 having attached to it a light guide (not specified in detail in FIG. 3) which introduces illumination radiation 25 into the mount 23.

The mount 23 guides (in a manner to be described in more detail below) the supplied illumination radiation 25 to the object field F so as to illuminate the latter sufficiently for observation through the observation microscope 20. In order to illustrate this, FIG. 3 schematically shows an illumination beam 26 incident on the iris 27 of the eye 2.

Like the contact glass 22, the observation microscope 20 is located on the optical axis A1 of the treatment apparatus 1. Thus, the contact glass 22 serves not only to guide the observation radiation of the observation microscope 20, but also to apply the treatment beam 4 as already generally explained above with respect to the adapter 12. The upper side 31 of the central region or of the contact glass 22 provides a known optical interface for the observation microscope 20.

FIG. 4 schematically shows the adapter 12 in a sectional view. As can be seen, the mount 23 holds the contact glass 22 and comprises a suction duct 28 at its lower side, said suction duct 28 allowing the mount 23 to be fixed on the cornea 17 by negative pressure. The contact glass 22 is glued into the mount 23 using an optically transparent glue whose refractive index is between that of the material of the contact glass 22 and that of the material of the mount 23. Thus, only minimal reflection losses occur where the radiation passes from the mount 23 into the contact glass 22.

By sucking the mount 23 onto the cornea 17, the lower side 30 of the contact glass 22 glued into the mount 23 is pressed onto the cornea 17 such that the desired intended shape 19 already explained above is ensured.

Instead of the two-part design according to FIG. 4, the adapter 12 may also be integrally provided as shown in FIG. 5. The mount 23 and the contact glass 22 are thus manufactured as one unitary part, e.g. by an injection molding method or by a machining method from an unmachined part. In principle, the presently described variants of the adapter 12 may be realized in multi-part form or in single-part form, in particular where the contact glass 22 and the mount 23 are concerned.

FIG. 6 shows an enlarged view of a detail of the contact glass 22 with the mount 23. Illumination beams 26 exiting at the coupler 24 are guided to the lower side 30 of the contact glass 22 by reflections and exit there in order to illuminate the object field. For this purpose, the mount 23 is provided with a reflecting circumferential surface 32 which is designed such that illumination beams 26 incident thereon appear below the Brewster angle and are thus reflected by total internal reflection.

In order to generate the illumination radiation, an illumination unit 33 is provided, comprising a thermionic emitter (light bulb) 34 or gas discharge unit, a luminescence diode or an LED for emitting the illumination radiation 25. The illumination radiation 25 is coupled into a light guide 36 via optics 35, said light guide 36 comprising a core 37 with a relatively high refractive index and a cladding 38 with a relatively low refractive index. Such light guides are known in the prior art. They guide the radiation in the light guide by total inner reflection. At its end, the light guide 36 is provided with a sleeve inserted into the coupler 24 such that the illumination radiation 25 is coupled from the light guide 36 into the mount 23 in the form of illumination radiation 26. The position of the coupler 24 shown in FIG. 6 is an example. The coupler may also be arranged elsewhere on the mount, e.g. at its periphery.

The illumination beams 26 impinge on the lower side 30 of the contact glass 22 after one or more reflections. In addition or as an alternative to the rim 32 provided at a suitable angle, suitable mirror coats may also be provided on the mount 23, e.g. in the region of the suction duct 28.

The exiting behavior of the illumination beams 26 at the lower side 30 depends quite substantially on whether the contact glass 22 contacts the eye or not. If the contact glass 22 does not (yet) contact the eye, the difference in refractive index between the contact glass 22 and the environment (usually air) is very great, and only beams impinging steeply on the interface 20 can leave the contact glass 22. However, if the contact glass 22 contacts the eye, the difference in refractive index is very small and only beams impinging very flatly on the interface 20 are reflected. Thus, the coupling of a considerable amount of radiation into the cornea 17 is effected only upon placing the contact glass 22 on the cornea 17.

FIG. 7 shows a sectional view similar to that of FIG. 6, with the illumination unit 33 not being illustrated here. As in the embodiment according to FIG. 6, the illumination radiation is also coupled into the contact glass 22 here from the mount 23 via the circumference. As a modification of the embodiment of FIG. 6, a duct 39 guiding radiation to the contact glass 22 is provided here in the mount 23. As material for the mount 23, non-transparent material is also suitable in this case. In order to couple the illumination radiation 25 into the duct 39, a lens 40 having a convex front surface 41 and a plane rear surface 42 is provided for the illumination radiation 25 which is emitted in a diverging manner at the light guide 36. Thus, following the lens 40 there are substantially paralleled illumination beams 26 which impinge at a defined angle on a mirror surface 43 provided in the duct 39. This results in the illumination beams 26 impinging on the lower side 30 of the contact glass 22 at a nearly uniform angle.

FIG. 8 shows a combination of the principles upon which the constructions of FIGS. 6 and 7 are based. An imaging entrance surface 44 is provided at the mount 23 here so as to collimate the illumination beams. Two mirror surfaces (not specified in detail) on the mount 23 in turn ensure the desired flat incidence on the lower side 30 of the contact glass 22.

The mirror surfaces provided in the mount 23 may have different designs according to the range of angles of incidence used. If the angles of incidence on these surfaces are large, e.g. nearly glancing, the surfaces may remain uncoated, and total internal reflection may be utilized. However, if the angles of incidence, as shown in FIG. 8, are rather such that incidence occurs close to vertical, reflectivity can be ensured by deposition of metallic or dielectric mirror coats. A further advantageous embodiment allows the interfaces which are designed merely as conical mirror surfaces in FIG. 8 to be provided with optical imaging properties. Also, the mirror surfaces may be surfaces located within the mount 23; they need not necessarily be located on the external surface as shown in FIG. 8.

FIG. 9 shows a further alternative embodiment of the adapter with illumination of the eye being effected here also already before positioning of the contact glass 22. For this purpose, the illumination beams 26, having been suitably collimated by an imaging entrance surface 44, exit at an exit surface 45 extending obliquely to the direction of beam propagation. The position of the exit surface 45 is selected such that the illumination beams 26 exit at the mount 23 as ray bundles 46 deflected in a direction toward a site B to be illuminated. The axis of the direction of propagation of the light bundle 46, said direction being defined by the exit surface 45, represents the optical axis of illumination. Thus, the direction of illumination can be selected such that it impinges on a predetermined site which is to be illuminated. During application in the LASIK method, the eye 2 can thus be illuminated during fitting of the contact glass.

The exit surface 45 may also have any predetermined curved design in order to impart a desired divergence to the bundle 42. This allows adjustment of the size of the illuminated site B. In order to be fixed to the eye 2, the mount 23 comprises a collar 47 at its lower side in the embodiment of FIG. 9, said collar forming the suction duct together with the exit surface 45.

The different constructions explained by way of example with reference to FIGS. 6 to 9 may, of course, be present at a mount 23 in plurality. Thus, it is quite possible and, for some illumination tasks, even particularly convenient to provide a plurality of coupling sites, i.e. couplers 24, so that illumination radiation is coupled in at a plurality of locations of the mount 23. There is no need for all of the various couplings to realize the same embodiment, e.g. one described with reference to FIGS. 6 to 9, but random combinations are also conceivable. For example, a construction for illumination of the eye 2 with the contact glass not yet in place, as described by way of example in FIG. 9, may be combined with constructions that couple illumination beams into the cornea 17 only upon positioning of the contact glass 22. This may be advantageous, in particular if the bundle 46 coupled into the suction duct via the exit surface 45 is not sufficient to illuminate the object field with the contact glass 22 in place. Such multiple illumination adapter allows illumination to be adapted according to the operation during application. For example, illumination may be effected according to the concept of FIG. 9 before the contact glass 22 is in place and according to one of the other concepts after it is in place. Control is conveniently effected by the control device 14.

Figure 10:
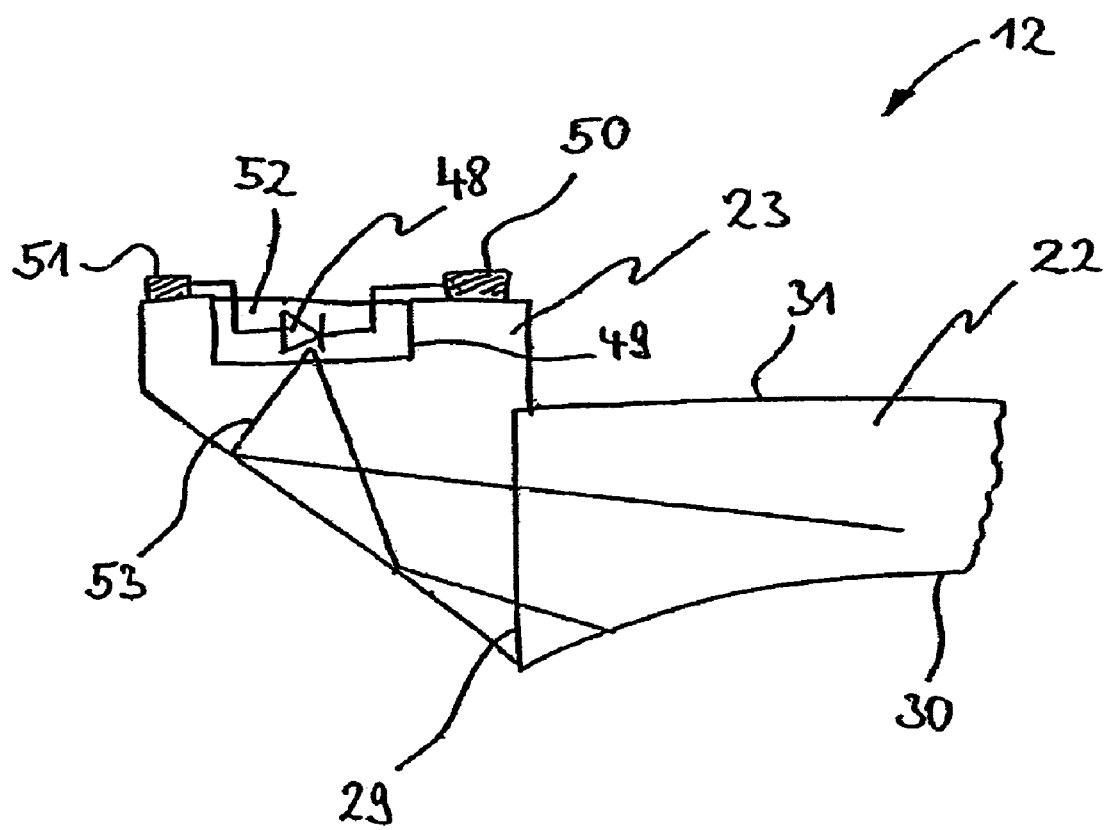
FIG. 10 shows an adapter for an ophthalmic method, with an LED as the source of illumination.

As an alternative to coupling the illumination radiation 25 in by means of one or more light guides 36, use may also be made of a mount 23 which is itself provided with means for generating the illumination radiation. One such example is represented in FIG. 10. The mount 23 is equipped with an LED 48 located in a recess 49 of the mount 23. The LED 48 is contacted via terminals 50 and 51.

The LED 48 is embedded in the recess 49 using a transparent curable material 52, e.g. an epoxy resin, which can be processed in the liquid state. The points of contact may be embodied as small contact pads or may extend around the entire circumference of the mount 23 in order to enable contact in any rotary position. In the case of contact pads, opposite annular contacts may also be used as an alternative in order to ensure contacting in any rotary position.

The path of the radiation 53 emitted by the LED 48 follows the principles represented with reference to FIGS. 6 to 9, i.e. the radiation 53 is irradiated onto the eye 2 directly from the mount 23 or is emitted at the lower side 30 via the contact glass 22. Of course, combinations are possible here, too.

The invention claimed is:

1. An adapter for coupling a laser processing device to an object, said adapter comprising:
   a central region movable into a laser beam path of a laser processing device;

an illumination beam path through which illumination radiation can be guided for illumination of an object field of an object, the object field coverable by said central region; and a peripheral region located outside said central region by which the adapter can be mounted on at least one of the object or the laser processing device, wherein said peripheral region is neither involved nor intended for imaging of said object field of said object, and wherein said illumination beam path is guided in said peripheral region and carries said illumination radiation, coupled into said peripheral region, to said object field in at least one of the following ways: directly and via said central region.

2. The adapter of claim 1, wherein said central region comprises a contact glass to be placed on the object and said peripheral region comprises a contact glass mount.

3. The adapter of claim 2, wherein an adhesive layer is provided between said contact glass mount and said contact glass, said adhesive layer having a refractive index intermediate the refractive index of said contact glass mount and said contact glass.

4. The adapter of claim 2, wherein said mount comprises a material transparent for illumination radiation, the material selected from the group consisting of: PMMA, polycarbonate, HW 55, and any combinations thereof.

5. The adapter of claim 1, further comprising a coupling unit for said illumination radiation, said coupling unit being provided at said peripheral region.

6. The adapter of claim 5, wherein said coupling unit comprises an imaging effect for said illumination radiation and comprises an interface selected from the group consisting of: a convex interface, a concave interface, a cylindrical interface, a toroidal interface, and any combinations thereof.

7. The adapter of claim 6, further comprising a reflecting surface and a plurality of coupling units, wherein said reflecting surface is segmented into facets and wherein each coupling unit has one or more of said facets assigned to it.

8. The adapter of claim 5, wherein said coupling unit comprises a dielectric layer for spectral filtering or reduction of reflections.

9. The adapter of claim 5, wherein said coupling unit comprises a LED mounted to or embedded in said peripheral region.

10. The adapter of claim 9, wherein annular contacts enabling contact to be made in any rotary position relative to the laser processing device are provided at said peripheral region.

11. The adapter of claim 1, wherein said peripheral region comprises an outside surface that reflects said illumination radiation.

12. The adapter of claim 11, wherein said reflecting surface has an imaging effect for said illumination radiation.

13. The adapter of claim 1, wherein said central and peripheral regions are integral.

14. An adapter for coupling a laser processing device to an object, said adapter comprising:

a central region movable into a laser beam path of a laser processing device;

an illumination beam path through which illumination radiation can be guided for illumination of an object field of an object, said object field coverable by said central region; and a peripheral region exterior said central region, wherein the adapter can be mounted on at least one of the object or the laser processing device, and wherein said illumination beam path can be guided in said peripheral region and carries said illumination radiation to said object field directly or through said central region and wherein said peripheral region is neither involved nor intended for imaging of said object field of said object.

15. The adapter of claim 14, wherein said central region comprises a contact glass operably coupleable to a contact glass mount provided at said peripheral region, and wherein an adhesive layer is provided between said contact glass mount and said contact glass, said adhesive layer having a refractive index intermediate the refractive index of said contact glass mount and said contact glass.

16. The adapter of claim 14, further comprising a coupling unit for said illumination radiation, said coupling unit being provided at said peripheral region.

17. The adapter of claim 16, wherein said coupling unit comprises an imaging effect for said illumination radiation and comprises an interface selected from the group consisting of: a convex interface, a concave interface, a cylindrical interface, a toroidal interface, and any combinations thereof.

18. The adapter of claim 17, further comprising a reflecting surface and a plurality of coupling units, wherein said reflecting surface is segmented into facets and wherein each coupling unit has one or more of said facets assigned to it.

19. The adapter of claim 14, wherein said peripheral region comprises an outside surface that reflects said illumination radiation, said outside surface comprising an imaging effect for said illumination radiation.

* * * * *